United States Patent [19]
Bäckström et al.

[11] Patent Number: 6,121,303
[45] Date of Patent: Sep. 19, 2000

[54] PHARMACOLOGICALLY ACTIVE CATECHOL DERIVATIVES

[75] Inventors: Reijo Bäckström, Helsinki; Erkki Honkanen, Espoo; Inge-Britt Linden, Helsinki; Erkki Nissinen, Espoo; Aino Pippuri, Espoo; Pentti Pohto, Espoo; Tapio Korkolainen, Helsinki, all of Finland

[73] Assignee: Orion-yhtymä Oy, Espoo, Finland

[21] Appl. No.: 09/261,460

[22] Filed: Feb. 23, 1999

Related U.S. Application Data

[60] Continuation of application No. 08/472,658, Jun. 7, 1995, Pat. No. 5,889,037, which is a division of application No. 08/325,024, Oct. 18, 1994, Pat. No. 5,614,541, which is a division of application No. 07/949,477, Oct. 23, 1992, Pat. No. 5,362,733.

[51] Int. Cl.$^7$ .................. A61K 31/4166; C07D 233/78; C07D 233/86; C07D 233/96

[52] U.S. Cl. .................. 514/389; 514/391; 544/299; 544/306; 548/146; 548/317.1; 548/321.5; 548/331.5; 548/333.1

[58] Field of Search .................. 548/317.1, 318.1, 548/319.1, 321.5, 146, 331.5, 333.1; 514/389, 391; 544/299, 306

[56] References Cited

U.S. PATENT DOCUMENTS

| | | | |
|---|---|---|---|
| 4,264,617 | 4/1981 | Bharucha et al. | 424/273 |
| 4,650,876 | 3/1987 | Mirviss | 548/308 |
| 5,208,250 | 5/1993 | Cetenko et al. | 514/369 |

*Primary Examiner*—Mukund J. Shah
*Assistant Examiner*—V. Balasubramanian
*Attorney, Agent, or Firm*—Burns, Doane, Swecker & Mathis, L.L.P.

[57] ABSTRACT

A compound of formula I

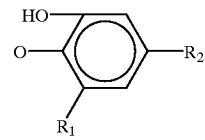

wherein $R_1$ is nitro, halogeno or cyano group and $R_2$ is a group selected from

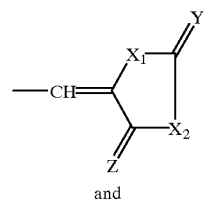

and

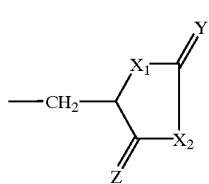

wherein Y and Z are independently oxygen, sulfur or NR, wherein R is hydrogen, straight or branched $C_{1-8}$alkyl, $C_{5-7}$cycloalkyl, phenyl$C_{1-8}$alkyl or phenyl group and $X_1$ and $X_2$ are NR, where R is hydrogen, straight or branched $C_{1-8}$ alkyl, $C_{5-7}$cycloalkyl, phenyl$C_{1-8}$alkyl or phenyl group, or a pharmaceutically acceptable salt or ester thereof. Pharmaceutical compositions are also disclosed.

11 Claims, No Drawings

PHARMACOLOGICALLY ACTIVE CATECHOL DERIVATIVES

This application is a continuation of application Ser. No. 08/472,658, filed Jun. 7, 1995 now U.S. Pat. No. 5,889,051, which is a divisional application of U.S. Ser. No. 08/325,024 filed on Oct. 18, 1994, now U.S. Pat. No. 5,614,541, which is a divisional application of U.S. Ser. No. 07/949,477, filed Oct. 23, 1992, now U.S. Pat. No. 5,362,733.

The invention relates to new catechol derivatives and pharmaceutically acceptable salts and esters thereof which are useful as medicinal antioxidants. The invention also relates to pharmaceutical compositions containing said compounds and to the method of the preparation of the same.

Medicinal antioxidants are compounds that may be used for the prevention or treatment of tissue damage induced by lipid peroxidation. It is generally believed that cellular damage by oxygen derived radicals, especially those associated with lipid peroxidation, is a significant factor in heart diseases, rheumatoid arthritis, cancer, certain inflammatory diseases, rejection reactions in transplantation, ischemia and even in the aging process.

EP-A-343643 described pharmaceutical compositions comprising the compounds of formula

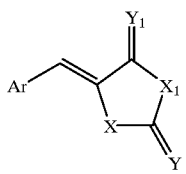

wherein Ar is (i) phenyl unsubstituted, (ii) phenyl substituted by from one to three of lower alkyl, lower alkoxy, hydroxy, halogen, trifluoromethyl, $NR_{10}R_{11}$, wherein $R_{10}$ and $R_{11}$ are independently hydrogen or lower alkyl, $NO_2$, mercapto, or lower alkylthio, (iii) naphthyl; (iv) benzofuranyl, (v) benzothiophenyl, (vi) 2- or 3-thienyl, (vii) 2- or 3-indolyl, (viii) 2- or 3-furanyl, or (ix) 2-, 3-, or 4-pyridyl Y and $Y_1$ is oxygen or sulfur; X is sulfur, oxygen, NH or $NCH_3$ and $X_1$ is NH or $NCH_3$ and pharmaceutically acceptable salts thereof which are stated to be 5-lipoxygenase and/or cyclooxygenase inhibitors. Japanese patent application No. 1052765, which has been referred to in Chemical Abstracts (CA 111(17)153788y) discloses thiazolidinone derivatives which are useful as aldose reductase inhibitors. Gupta et al. in Eur. J. Med. Chem.—Chim. Ther., 17 (5), 448–52, 1982 and Srivastava et al. in Pharmazie, 36(4), 252–3, 1981 disclose 2-thioxo-4,6-pyrimidinedione compounds having anticonvulsant activity. Sohda et al. in Chem. Pharm. Bull., 31(2), 560–9, 1983 discloses 2,4-thioxolidione derivatives having antiulcer activity.

The compounds of the present invention may be represented by the formula I

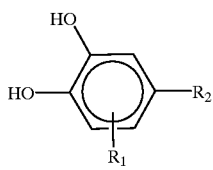

wherein $R_1$ is an electronegative substituent such as nitro, halogeno or cyano group and $R_2$ is a group selected from

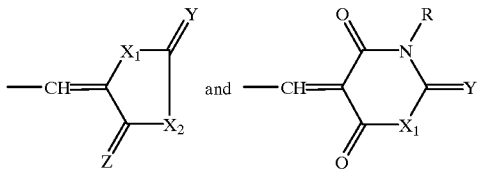

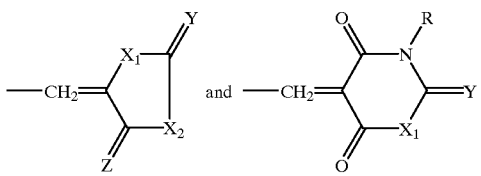

wherein R is hydrogen, or an alkyl, cycloalkyl, aralkyl or aryl group, wherein $X_1$, $X_2$, Y and Z are independently oxygen, sulfur or NR wherein R may be as defined above. In one embodiment, $R_2$ is a group containing a five membered heterocyclic ring which is of formula

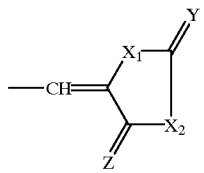

in which $X_1$ and $X_2$ are both NR, wherein R is hydrogen or alkyl, Y is oxygen or sulfur and Z is oxygen or sulfur. Preferred ring systems include 2-thioxoimidazolidin-5-ones and 2,5-imidazolidin-5-ones. Examples of such compounds include 4-[(3,4-dihydroxy-5-nitrophenyl)methylidene]-2-thioxoimidazolidin-5-one; 4-[(3,4-dihydroxy-5-chlorophenyl)methylidene]-2-thioxoimidazolidin-5-one; 4-[(3,4-dihydroxy-5-nitrophenyl)methylidene]-2,5-imidazolidindione and 4-[(3,4-dihydroxy-5-cyanophenyl) methylidene]-2-thioxoimidazolidin-5-one.

In another embodiment $R_2$ is the group

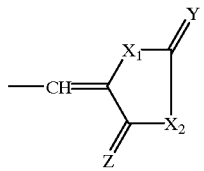

in which $X_1$, Y, and Z are independently oxygen or sulfur and $X_2$ is NR, in which R is hydrogen or alkyl. Preferred ring systems include 2-thioxothiazolidin-4-ones; 3-methyl-2-thioxothiazolidin-4-ones; thiazolidin-2,4-diones; 4-thioxo-2-oxazolidinones and 4-thioxithiazolidin-2-ones. Specific examples are 5-[(3,4-dihydroxy-5-nitrophenyl) methylidene]-2-thioxothiazolidin-4-one; 5-[(3,4-dihydroxy-5-nitrophenyl)methylidene]-3-methyl-2-thioxothiazolidin-4-one; 5-[(3,4-dihydroxy-5-nitrophenyl)methylidene] thiazolidin-2,4-dione; 5-[(3,4-dihydroxy-5-chlorophenyl) methylidene]-thiazolidin-2,4-dione; 5-[(3,4-dihydroxy-5-nitrophenyl)methylidene]-4-thioxo-2-oxazolidinone; 5-[(3, 4-dihydroxy-5-nitrophenyl)methylidene]-4-thioxothiazolidin-2-one and 5-[(3,4-dihydroxy-5-cyanophenyl)methylidene]-2-thioxothiazolidin-4-one.

In another embodiment $R_2$ is the group

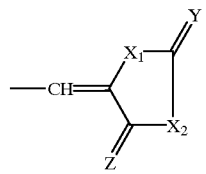

in which $X_1$ and Z are independently oxygen or sulfur and Y and $X_2$ are NR, wherein R is hydrogen. Preferred ring system is 2-aminothiazolidin-4-one. A specific example is 5-[(3,4-dihydroxy-5-nitrophenyl)methylidene]-2-aminothiazolidin-4-one.

In another embodiment $R_2$ is a group containing a six-membered heterocyclic ring which is of formula:

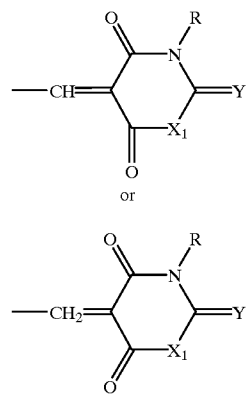

wherein Y is oxygen or sulfur, $X_1$ is NR, wherein R is hydrogen or alkyl. Preferably Y is oxygen. Preferred ring systems include pyrimidine-2,4,6-trione. Examples of such compounds include 5-[(3,4-dihydroxy-5-nitrophenyl) methylidene]-2,4,6 (1H,3H,5H)-pyrimidinetrione and 5-[(3,4-dihydroxy-5-nitrophenyl)methyl]-(1H,3H,5H)-pyrimidine-2,4,6-trione.

The term "alkyl" as employed herein by itself or as part of another group refers to both straight and branched chain groups, preferably of 1 to 8 atoms, most preferably of 1 to 4 carbon atoms.

The term "aryl" as employed herein refers to a monocyclic or bicyclic group containing 6 or 10 carbon atoms in the ring portion. A specific example is phenyl.

The term "acyl" as employed herein refers to alkylcarbonyl group, the alkyl group being as defined above.

The term "aroyl" refers to an arylcarbonyl group, the aryl group being defined above.

The term "cycloalkyl" as employed herein refers to saturated cyclic hydrocarbon groups having preferably 5 to 7 carbon atoms.

The term "halogeno" as employed herein refers to fluoro, chloro, bromo or iodo substituent. Especially preferred is chloro.

If R is hydrogen the compounds of the present invention may exist also in the corresponding tautomeric forms depending on the pH of the solution.

Thus, when $R_2$ is a five-membered ring, when $X_1$ is NR wherein R is hydrogen the tautomeric forms of the compounds according to formula Ia are

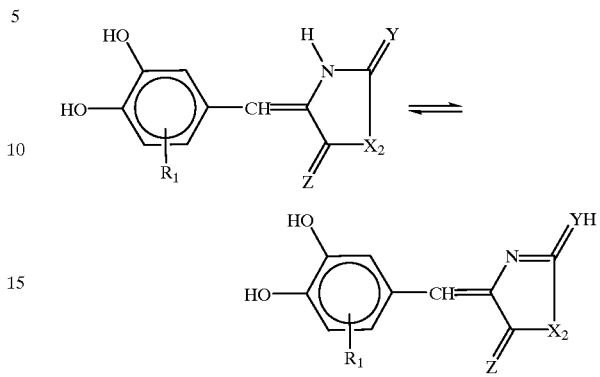

and the tautomers, when $X_2$ is NR wherein R is hydrogen are

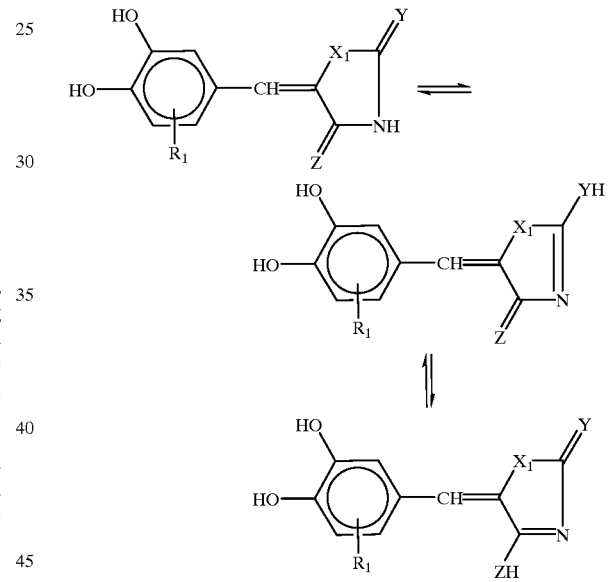

The tautomeric forms for the compounds wherein $R_2$ is a six membered ring are respectively

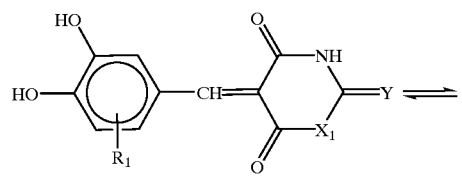

-continued

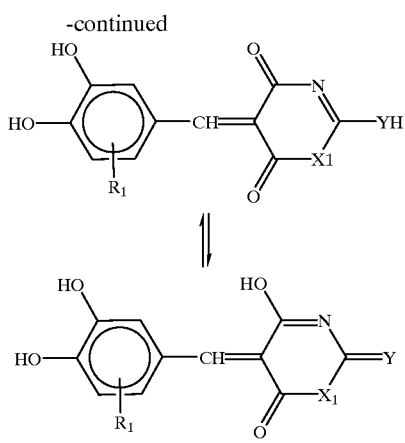

The present invention also relates to the method for the preparation of compounds of formula I. The present invention provides a process for the preparation of compounds of formula I, in which process an aldehyde of formula II

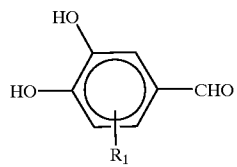
II wherein $R_1$ is as defined above, is condensed in a base or acid catalyzed reaction with compounds of either formulas III or IV having an active methylene group

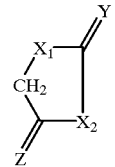
III

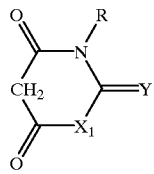
IV wherein $X_1$, $X_2$, Y and Z are as defined above, to give a compound Ia according to the present invention, whereafter the carbon-carbon double bond in Ia may be reduced to give the compound Ib according to the invention.

The invention also relates to pharmaceutically acceptable salts and esters of the present compounds. Generally, the esters which hydrolyze readily in physiological circumstances are those attached to the phenolic hydroxyl groups in compounds according to formula I. Either one of the hydroxylic groups or both of them may be esterified and on hydrolyzing the ester-forming group or groups are cleaved away and the active compound is liberated. Preferred esters are acyl or aroyl derivatives.

Salts of the compounds, when applicable, may be prepared by known methods. Physiologically acceptable salts are useful as active medicaments. However, sodium, potassium, ammonium, calcium and magnesium salts are preferred.

The effective dose of the compound varies considerably depending on whether the compounds are given for prophylaxis or for treatment, the severity of the condition to be treated, and the route of administration. The effective dose for human beings is likely to be from about 1 to 1000 mg per day.

The compounds used in this invention are formulated into dosage forms using the principles which are known to the man having average skill in the art. The compounds according to this invention are given to a patient as such or in combination with suitable pharmaceutical material in the form of tablets, dragees, capsules, suppositories, emulsions, suspensions or solutions whereby the content of the active compound is in the formulation from 1 to 100 weight %.

Choosing the auxiliary ingredients for the formulation is routine for those of ordinary skill in the art. It is evident that suitable solvents, gel forming ingredients, dispersion forming ingredients, colors etc are used in a normal way.

The compositions may be administered enterally or parenterally.

Test Results

Radical Trapping Capacity of Compounds

The tested compounds were subjected to controlled peroxidation by peroxylradicals originating from the thermal decomposition of 2,2'-azobis-(2-amidinopropane)×HCl at 37° C. The rate of radical formation was followed by luminol enhanced chemiluminescence (CL). From the duration of CL and from the fact that the phenolic antioxidant vitamin E analogue TROLOX® traps two radicals (Barclay, L. et al., J. Am. Chem. Soc. 106: 2479–2481, 1984) the stochiometric factors were calculated. The results are presented in Table 1.

TABLE 1

The binding of peroxyl radicals by various test compounds

| Compound | Stochiometric factor |
|---|---|
| 1 | 7.1 |
| 2 | 5.6 |
| 3 | 4.7 |
| 4 | 4.4 |
| 5 | 4.2 |
| 6 | 4.0 |
| 7 | 4.0 |
| TROLOX | 2.0 |
| Ascorbic acid | 0.7 |

1 4-[(3,4-dihydroxy-5-chlorophenyl)methylidene]-2-thioxo-imidazolidin-5-one
2 5-[(3,4-dihydroxy-5-cyanophenyl)methyildene]-2-thioxo-thiazolidin-4-one
3 4-[(3,4-dihydroxy-5-nitrophenyl)methylidene]-2,5-imid-azolindione
4 5-[(3,4-dihydroxy-5-nitrophenyl)methylidene]-2-thioxo-thiazolidin-4-one
5 4-[(3,4-dihydroxy-5-nitrophenyl)methylidene]-2-thioxo-imidazolidin-5-one
6 5-[(3,4-dihydroxy-5-nitrophenyl)methylidene]-2,4,6(1H, 3H, 5H)-pyrimidinetrione
7 4-[(3,4-dihydroxy-5-cyanophenyl)methylidene]-2-thioxo-imidazolidin-5-one The following examples illustrate the preparation of the compounds according to the invention.

EXAMPLE 1

4-[(3,4-Dihydroxy-5-nitrophenyl)methylidene]-2-thioxoimidazolidin-5-one

A solution containing 2.9 g (0.025 mol) of 2-thiohydantoin, 4.6 g (0.025 mol) of 3,4-dihydroxy-5- nitrobenzaldehyde and 0.25 ml of piperidine in 50 ml of acetic acid was heated for 7–8 h at 100° C. The crystals were filtered and washed with 2-propanol. Yield 5.0 g (71%), mp>350° C. (decom.).

EXAMPLE 2

5-[(3,4-Dihydroxy-5-nitrophenyl)methylidene]-2-thioxothiazolidin-4-one

A solution containing 2.1 g (0.0157 mol) of rhodanine, 2.76 g (0.0151 mol) of 3,4-dihydroxy-5-nitrobenzaldehyde and 0.15 ml of piperidine in 10 ml of acetic acid was heated for 7–8 h at 100° C. After cooling the crystals were filtered and washed with 2-propanol. Yield 4.0 g (89%), mp>350° C. (decomp.).

EXAMPLE 3

5-[(3,4-Dihydroxy-5-nitrophenyl)methylidene]-thiazolidin-2,4-dione

A solution containing 0.59 g (0.005 mol) of thiazolidine-2,4-dione, 0.92 g (0.005 mol) of 3,4-dihydroxy-5-nitrobenzaldehyde and 0.05 ml of piperidine in 5 ml of acetic acid was heated for 7–8 h at 80° C. The crystals were filtered and washed with ethanol. Yield 1.0 g (72%), mp 295–298° C.

EXAMPLE 4

5-[(3,4-Dihydroxy-5-nitrophenyl)methylidene]-2-aminothiazolidin-4-one

A solution containing 0.58 g (0.005 mol) of 2-aminothiazolidin-4-one, 0.92 g (0.005 mol) of 3,4-dihydroxy-5-nitrobenzaldehyde and 0.05 ml of piperidine in 5 ml of acetic acid was heated for 24 h at 100° C. The product was filtered and washed with ethanol. Yield 1.2 g (86%), mp 250° C. (decomp.).

EXAMPLE 5

5-[(3,4-Dihydroxy-5-nitrophenyl)methylidene]-4-thioxothiazolidin-2-one

A solution containing 0.67 g (0.005 mol) of 4-thioxothiazolidin-2-one, 0.92 g (0.005 mol) of 3,4-dihydroxy-5-nitrobenzaldehyde and 0.05 ml of piperidine in 10 ml of acetic was heated for 8 h at 100° C. The product was filtered and washed with 2-propanol. Yield 1.14 g (76.5%), mp >350° C. (decomp.).

EXAMPLE 6

5-[(3,4-Dihydroxy-5-nitrophenyl)methylidene]-3-methyl-2-thioxothiazolidin-4-one

A solution containing 0.74 g (0.005 mol) of 3-methyl-2-thioxothiazolidin-4-one, 0.92 g (0.005 mol) of 3,4-dihydroxy-5-nitrobenzaldehyde, 0.05 ml of piperidine in 10 ml of acetic acid was heated for 8 h at 100° C. The product was filtered and washed with 2-propanol. Yield 0.87 g (56%), mp 274–276° C.

EXAMPLE 7

5-[(3,4-Dihydroxy-5-nitrophenyl)methylidene]-2,4,6 (1H,3H,5H)pyrimidinetrione

To a solution containing 1.28 g (0.01 mol) of barbituric acid and 1.83 g (0.01 mol) of 3,4-dihydroxy-5-nitrobenzaldehyde in 20 ml of 2-propanol was gradually added 5.0 ml of thionyl chloride. The mixture was stirred for 100 h at room temperature. The product was filtered, washed with 2-propanol and recrystallized from acetic acid. Yield 1.28 g (44%), mp 269–272° C.

EXAMPLE 8

4-[(3,4-Dihydroxy-5-nitrophenyl)methylidene]-2,5-imidazolidindione

A solution containing 0.65 g of hydantoin, 0.92 g of 3,4-dihydroxy-5-nitrobenzaldehyde and 0.15 g of ammonium acetate in 15 ml of acetic acid was refluxed overnight. The product was filtered and washed with acetic acid and 2-propanol. Yield 0.56 g (42%), mp>350° C.

EXAMPLE 9

5-[(3,4-Dihydroxy-5-nitrophenyl)methylidene]-4-thioxo-2-oxazolidinone

A solution containing 0.25 g of 4-thioxo-2-oxazolone 0.38 g of 3,4-dihydroxy-5-nitrobenzaldehyde and 0.1 ml of piperidine in 5 ml of acetic acid was heated overnight at 100° C. The product was filtered and washed with actic acid. Yield 0.05 g, mp 245° C.

EXAMPLE 10

4-[(3,4-Dihydroxy-5-cyanophenyl)methylidene]-2-thioxoimidazolidin-5-one

A solution containing 0.58 g of thiohydantoin, 0.82 g of 3,4-dihydroxy-5-cyanobenzaldehyde and 0.1 ml of piperidine in 10 ml of acetic acid was heated for 4 h at 100° C. The product was filtered and washed with ether. Yield 0.51 g, mp 210–213° C.

EXAMPLE 11

5-[(3,4-Dihydroxy-5-cyanophenyl)methylidene]-2-thioxothiazolidin-4-one

A solution containing 0.61 g of rhodanine, 0.72 g of 3,4-dihydroxy-5-cyanobenzaldehyde and 0.1 ml of piperidine in 10 ml of acetic acid was heated for 4 h at 100° C. The product was filtered and washed with 2-propanol. Yield 0.35 g, mp>350° C.

EXAMPLE 12

4-[(3,4-Dihydroxy-5-chlorophenyl)methylidene]-2-thioxoimidazolidin-5-one

A solution containing 1.16 g of thiohydantoin, 1.72 g of 3,4-dihydroxy-5-chlorobenzaldehyde and 0.2 ml of piperidine in 20 ml of acetic acid was heated for 4 h at 100° C. The product was filtered and washed with ether. Yield 1.0 g, mp 303–304° C.

EXAMPLE 13

5-[(3,4-Dihydroxy-5-chlorophenyl)methylidene]-thiazolidin-2,4-dione

A solution containing 1.33 g of thiazolidine-2,4-dione, 1.72 g of 3,4-dihydroxy-5-chlorobenzaldehyde and 2 ml of piperidine in 20 ml of acetic acid was heated for five hours at 100° C. Yield 1.9 g (70%), mp 299–301° C.

EXAMPLE 14

5-[(3,4-Dihydroxy-5-nitrophenyl)methyl]-(1H,3H, 5H)pyrimidine-2,4,6-trione

To a suspension of 5-[(3,4-dihydroxy-5-nitrophenyl) methylidene]-(1H,3H,5H)pyrimidine-2,4,6-trione (Example 7) (1 g) in water (30 ml) a solution of sodiumborohydride (2 g) in water (10 ml) was gradually added. The solution was stirred for 15 min at room temperature and acidified with 1 N hydrochloric acid. The product was filtered and washed with water. Yield 0.7 g, mp 263–6° C.

What is claimed is:

1. A compound according to formula I

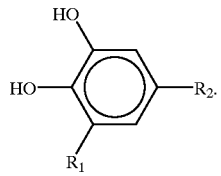

wherein $R_1$ is nitro, halogeno or cyano group and $R_2$ is a group selected from

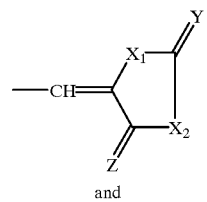

and

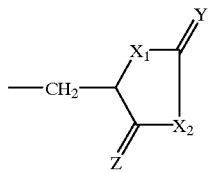

wherein Y and Z are independently oxygen, sulfur or NR, wherein R is hydrogen, straight or branched $C_{1-8}$ alkyl, $C_{5-7}$cycloalkyl, phenyl$C_{1-8}$alkyl or phenyl group and $X_1$ and $X_2$ are NR, where R is hydrogen, straight or branched $C_{1-8}$alkyl, $C_{5-7}$cycloalkyl, phenyl$C_{1-8}$alkyl or phenyl group, or a pharmaceutically acceptable salt or ester thereof.

2. The compound as claimed in claim 1, wherein $R_1$ is cyano.

3. The compound as claimed in claim 1, wherein $R_1$ is nitro.

4. The compound as claimed in claim 1, wherein $R_1$ is halogeno.

5. The compound as claimed in claim 1, wherein in the compound of formula I, $R_2$ is a group according to formula Ia,

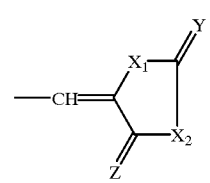

in which $X_1$ and $X_2$ are both NR, wherein R is hydrogen or $C_{1-8}$alkyl, Y is oxygen or sulfur and Z is oxygen.

6. The compound as claimed in claim 5, which is

4-[(3,4-dihydroxy-5-nitrophenyl)methylidene]-2,5-imidazolidindione or the pharmaceutically acceptable salts and esters thereof.

7. The compound as claimed in claim 1, wherein the compound of formula I, $R_2$ is a group according to formula Ia, in which $X_1$ and $X_2$ are both NR, wherein R is hydrogen or $C_{1-8}$ alkyl, Y is sulfur and Z is oxygen.

8. The compound according to claim 7, which is

4-[(3,4-dihydroxy-5-nitrophenyl)methylidene]-2-thioxoimidazolidin-5-one or the pharmaceutically acceptable salts and esters thereof.

9. The compound according to claim 7, which is

4-[(3,4-dihydroxy-5-chlorophenyl) methylidene]-2-thioxoimidazolidin-5-one or the pharmaceutically acceptable salts and esters thereof.

10. The compound according to claim 7, which is

4-[(3,4-dihydroxy-5-cyanophenyl)methylidene]-2-thioxoimidazolidin-5-one or the pharmaceutically acceptable salts and esters thereof.

11. A pharmaceutical composition for use in the prevention or treatment of tissue damage induced by lipid peroxidation, said composition comprising an effective antioxidant amount of a compound as claimed in claim 1 and a pharmaceutically acceptable carrier or diluent therefor.

* * * * *